United States Patent
Bai et al.

(10) Patent No.: US 11,175,418 B2
(45) Date of Patent: Nov. 16, 2021

(54) HANDLING DETECTOR PIXEL PERFORMANCE VARIATION IN DIGITAL POSITRON EMISSION TOMOGRAPHY

(71) Applicant: KONINKLIJKE PHILIPS N.V., Eindhoven (NL)

(72) Inventors: Chuanyong Bai, Solon, OH (US); Andriy Andreyev, Willoughby Hills, OH (US); Shushen Lin, Cleveland, OH (US); Bin Zhang, Highland Heights, OH (US); Michael Allen Miller, Cleveland Heights, OH (US); Xiyun Song, Cupertino, CA (US); Jinghan Ye, Livermore, CA (US); Shekhar Dwivedi, Willoughby Hills, OH (US); Zhiqiang Hu, Twinsburg, OH (US); Yu-Lung Hsieh, Aurora, OH (US); Ilya Brodskiy, Richmond Heights, OH (US); Thomas Christopher Bulgrin, Columbia Station, OH (US); Yang-Ming Zhu, Wilmington, MA (US); Douglas B. McKnight, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/649,416

(22) PCT Filed: Sep. 12, 2018

(86) PCT No.: PCT/EP2018/074546
§ 371 (c)(1),
(2) Date: Mar. 20, 2020

(87) PCT Pub. No.: WO2019/057572
PCT Pub. Date: Mar. 28, 2019

(65) Prior Publication Data
US 2020/0301032 A1    Sep. 24, 2020

Related U.S. Application Data

(60) Provisional application No. 62/561,706, filed on Sep. 22, 2017.

(51) Int. Cl.
*G01T 7/00* (2006.01)
*A61B 6/03* (2006.01)
(Continued)

(52) U.S. Cl.
CPC .............. *G01T 7/005* (2013.01); *A61B 6/037* (2013.01); *A61B 6/585* (2013.01); *G01T 1/2985* (2013.01); *G06T 11/005* (2013.01)

(58) Field of Classification Search
CPC ..... G01T 7/005; G01T 1/2985; G06T 11/005; A61B 6/585; A61B 6/037
See application file for complete search history.

(56) References Cited

U.S. PATENT DOCUMENTS

| | | | | |
|---|---|---|---|---|
| 6,457,861 | B1 * | 10/2002 | Petrick | A61B 6/032 378/207 |
| 2002/0065611 | A1 * | 5/2002 | Boehm | A61B 6/585 702/35 |

(Continued)

FOREIGN PATENT DOCUMENTS

| | | |
|---|---|---|
| WO | 03001243 A2 | 1/2003 |
| WO | 2014001926 A1 | 1/2014 |

OTHER PUBLICATIONS

International Search Report dated Feb. 25, 2019.
(Continued)

*Primary Examiner* — Michael C Bryant (57) ABSTRACT

A non-transitory computer-readable medium storing instructions readable and executable by a workstation (18) including at least one electronic processor (20) to perform a quality control (QC) method (100). The method includes: receiving a current QC data set acquired by a pixelated detector (14) and one or more prior QC data sets acquired by the pixelated detector; determining stability levels of detector pixels (16)

(Continued)

of the pixelated detector over time from the current QC data set and the one or more prior QC data sets; labeling a detector pixel of the pixelated detector as dead when the stability level determined for the detector pixel is outside of a stability threshold range; and displaying, on a display device (24) operatively connected with the workstation, an identification (28) of the detector pixels labelled as dead.

20 Claims, 3 Drawing Sheets

(51) Int. Cl.
*G01T 1/29* (2006.01)
*A61B 6/00* (2006.01)
*G06T 11/00* (2006.01)

(56) References Cited

U.S. PATENT DOCUMENTS

2013/0184537 A1 7/2013 Konuma
2017/0115409 A1* 4/2017 Laurence ............... G01T 7/005

OTHER PUBLICATIONS

Anwen Long, Qiude Zhang, Zhangjing Xiiong, Peng Xiao and Qingguo Xie, "Energy Calibration Method for an All-Digital High Resolution Gamma-Ray Spectroscopy", 2014 IEEE NUC Science Symposium.

* cited by examiner

HANDLING DETECTOR PIXEL PERFORMANCE VARIATION IN DIGITAL POSITRON EMISSION TOMOGRAPHY

CROSS-REFERENCE TO PRIOR APPLICATIONS

This application is the U.S. National Phase application under 35 U.S.C. § 371 of International Application No. PCT/EP2018/074546, filed on Sep. 12, 2018, which claims the benefit of U.S. Provisional Application No. 62/561,706, filed on Sep. 22, 2017. These applications are hereby incorporated by reference herein.

FIELD

The following relates generally to the medical imaging arts, medical image interpretation arts, image reconstruction arts, medical imaging device maintenance arts, and related arts.

BACKGROUND

Digital positron emission tomography (PET) detectors include an assembly of a large number of pixels. In one pixelated detector design, each detector pixel is a small scintillator crystal cut to the desired size and has an associated scintillation light detection unit and electronics to detect 511 keV gamma rays in a PET scan. The crystal preparation, detector assembling process, and the like are kept as systematic as possible so that the performance of most of the pixels are relatively similar and predictable, thereby forming the major subset of average pixels.

A small portion of the detector pixels may be significantly different than the average pixels due to many reasons, such as crystal non-uniformity, manufacturing processing variation, photon detection unit (e.g., photodiode) performance fluctuation, assembly process inconsistence, electronics variation, and the like. Some of such pixels have sensitivity much lower than the average pixels. Some of such pixels have sensitivity much higher than the average; and still some pixels may have unstable sensitivity. That is, there sensitivity varies from time to time, either dramatically or continuously.

Assessment of detector pixel performance is typically performed by way of a detector pixel calibration involving acquisition of events data from a standard uniform phantom preferably placed at the scanner isocenter so as to be equidistant from the detectors of a detector ring. Due to the time and effort involved, pixel calibration is usually performed infrequently, e.g. only after major maintenance or the like. The calibration typically also includes determining normalization factors for the detector pixels to account for differences in sensitivity of individual pixels.

In some existing PET systems, pixels with extremely low sensitivity (e.g., a low limit being 20% or less of the sensitivity of the average pixels) and pixels with artificially high sensitivity (e.g., a high limit being 40% higher than the average pixels) are deemed as dead pixels. When pixels are identified as dead, they are excluded from the data processing as if they don't exist. For example, the events associated with dead pixels are excluded from the system performance evaluations, such as National Electrical Manufacturer's Association (NEMA) sensitivity, count rate performance evaluation, as well as being excluded from the image reconstruction process (such as list-mode iterative reconstruction, for example). In reconstruction, approaches for handling dead pixels are sometimes employed to minimize the negative impact of dead pixels in image quality (e.g., resolution, artifacts etc.) and quantitative accuracy (e.g., lesion intensity, SUV, etc.).

These approaches for dealing with atypical detector pixels have some drawbacks. For instance, unstable pixels, having a sensitivity fluctuating with time between the low and high limits, can be difficult to identify. If the pixel has sensitivity varying between, for example, 20% and 140% of the average pixels, the calibration of the PET system may not detect such pixels since the calibration is performed infrequently and does not track performance with high temporal resolution. Normalization can implicitly compensate such variation, but any pixel performance variation occurs between two normalizations cannot be detected and compensated.

If a group of clustered pixels (e.g., a tile, a module, and the like) have very low sensitivity (e.g., 50% of the average) or their sensitivity is much different than other pixels, they can introduce significant image artifacts and quantitative errors in certain situations. Such a situation can arise if the root cause of the sensitivity variation is at the tile or module level, e.g. a problem with the tile or module electronics that impacts all detectors of the tile or module. The normalization process can implicitly compensate such tile- or module-level variation, but the normalization is performed infrequently. If the sensitivity variation of the tile or module occurs between two normalizations, then patient data may be compromised, and the resulted images may have artifacts and quantitative errors.

Existing approaches which label pixels as dead can also be over-inclusive, so as to exclude useful imaging data. If pixels labeled as dead are stable over the duration of the scan, the counts associated with these dead pixels may still be useful. In fact, such counts can be very valuable in low dose studies, short scans, or dynamic scans. However, the existing approaches exclude counts from dead pixels from being used.

When the number of dead pixels increases and/or they become clustered, users may get worried as to whether the system is still safe to use. Guidelines for service calls may not be sufficient for those sophisticated users, possibly leading to unnecessary or premature maintenance calls. Conversely, less attentive users may fail to recognize the number of dead pixels is becoming high enough to adversely impact clinical imaging quality.

The following discloses new and improved systems and methods to overcome these problems.

SUMMARY

In one disclosed aspect, a non-transitory computer-readable medium stores instructions readable and executable by a workstation including at least one electronic processor to perform a quality control (QC) method. The method includes: receiving a current QC data set acquired by a pixelated detector and one or more prior QC data sets acquired by the pixelated detector; determining stability levels of detector pixels of the pixelated detector over time from the current QC data set and the one or more prior QC data sets; labeling a detector pixel of the pixelated detector as dead when the stability level determined for the detector pixel is outside of a stability threshold range; and displaying, on a display device operatively connected with the workstation, an identification of the detector pixels labelled as dead.

In another disclosed aspect, an imaging system includes an image acquisition device configured to acquire imaging data of a patient, the image acquisition device including a pixelated detector with a plurality of detector pixels, and a display device. At least one electronic processor is programmed to: receive a current quality control (QC) data set acquired by the pixelated detector and one or more prior QC data sets acquired by the pixelated detector; determine stability levels of the detector pixels over time from the current QC data set and the one or more prior QC data sets; label one or more of the detector pixels as dead when the stability level determined for the detector pixels is outside of a stability threshold range; and control the display device to display an identification of the detector pixels labelled as dead.

In another disclosed aspect, an imaging system includes a positron emission tomography (PET) device configured to acquire imaging data of a patient. The image acquisition device includes a PET detector ring with a plurality of PET detector pixels. The imaging system also includes a display device. At least one electronic processor is programmed to: receive a current quality control (QC) data set acquired by the pixelated detector and one or more prior QC data sets acquired by the pixelated detector; determine sensitivity levels of the detector pixels from the current QC data set; determine stability levels of the detector pixels over time from the current QC data set and the one or more prior QC data sets; label a detector pixel of the pixelated detector as dead when the sensitivity level is above a maximum sensitivity threshold; label a detector pixel of the pixelated detector as cold when the sensitivity level is below a minimum sensitivity threshold; and control the display device to display an identification of the detector pixels labelled as dead or cold.

One advantage resides in more effective and timely identification of unstable detector pixels.

Another advantage resides in identifying previously unstable detector pixels that have re-stabilized.

Another advantage resides in reconstructing imaging data including data acquired using detector pixels with a low, but stable, sensitivity level.

Another advantage resides providing a clinician with an identification of detector pixels labeled as dead.

Another advantage resides in more effectively informing a clinician of the effect of dead detector pixels on clinical image quality.

Another advantage resides in reducing maintenance calls for PET detector ring maintenance issues.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

In existing digital PET imaging device maintenance, a detector pixel normalization calibration is performed infrequently, e.g. after major maintenance or on a schedule with long (e.g. multi-month) intervals between calibrations. The normalization involves acquiring data from a standard uniform phantom. During the normalization calibration, any pixels with sensitivity below a minimum threshold ("cold" pixels) are labeled as dead, and similarly any pixels with sensitivity above a maximum threshold ("hot" pixels) are also labeled as dead pixels. The rationale is that the cold pixels are most likely missing many counts, while the hot pixels are producing many spurious counts. Counts acquired using pixels labeled as dead pixels are ignored, and the sensitivity matrix used in the iterative image reconstruction is adjusted to account for the missing pixels.

Additionally, a daily quality control (QC) procedure is typically performed using a standard point source phantom, e.g. a $^{22}$Na point source. The QC checks various detector pixel parameters, such as energy resolution, detector uniformity, and also detects dead pixels. The information generated from the QC procedure is not used to adjust any scanner settings, but only to verify the scanner is operating within an acceptable envelope. If, for example, the QC detects too many dead pixels, this may result in a maintenance call.

Embodiments disclosed herein advantageously leverage the existing QC procedure to assess the day-to-day stability of the detector pixels. In some contemplated implementations, this additional QC information is informational, i.e. dead pixels are detected based on the sensitivity thresholds or based on instability, and if there are too many dead pixels this may trigger a maintenance call or a new normalization calibration.

In other embodiments disclosed herein, the information obtained from the QC data may be used to label unstable detector pixels as dead, and/or to re-label pixels currently labeled as dead to be live pixels. In one illustrative process, the labeling includes: (1) labeling any unstable pixel as dead even if its sensitivity is within the lower/upper threshold bounds; (2) label any pixel whose sensitivity is over threshold as dead; and (3) label any stable pixel whose sensitivity is under threshold as live.

In another disclosed aspect, the effect of newly identified dead pixels may be simulated to inform the user as to the practical clinical effect of these dead pixels. This simulation can be done in a straightforward way: an existing phantom or clinical image is compared with the original dataset whose reconstruction is repeated with any counts due to the newly identified dead pixels removed (and the sensitivity matrix used in the image reconstruction adjusted appropriately). In addition to simulating the existing population of dead pixels, simulations are contemplated to be done for forecasts of additional dead pixels to inform the user of when the dead pixel count becomes problematic from a clinical viewpoint. If this is done for actual clinical images, the impact is to provide clinicians with a real-world forecast of the impact of dead pixels on clinical imaging of the type actually performed at the hospital.

In some instances, the acquired data can be saved in a performance map. For example, in the daily QC data collection, the pixel performance map can be obtained using coincidence counts. For existing PET systems, to avoid the geometric response variation and shadowing of the normal crystals opposite to the real dead pixels, one can alternatively use singles (i.e., single 511 keV gammas) of each pixel to obtain the pixel performance map. Since the pixel performance map is obtained daily, the analysis of pixel performance is also performed daily. The application of such a map in data processing can provide assurance of the trustworthiness of the acquired data from day to day. Thus, the risk is minimized even though intra-day variance cannot be detected and handled. This day-to-day process makes daily pixel sensitivity normalization calibration procedure unnecessary, thereby significantly saving time and expense (e.g., phantom, source, etc.) for daily operation.

A typical image reconstruction process implemented by existing PET systems uses the detector normalization results to implicitly handle pixel performance variance. However, the normalization is not performed daily as it is a time consuming process due to a need to fill a uniform phantom with activity and perform the scan and analysis. In methods and systems disclosed herein, pixel performance variance occurring between successive normalizations is detected in a daily basis, and applying the resultant performance map in the image reconstruction can improve data fidelity and minimize the risks of data compromise. In these processes, intermittent (i.e. unstable) pixels are excluded from data processing. Any adjustment in individual pixel sensitivity that proves to be stable over time is included in a projection/backprojection model of the iterative reconstruction algorithm, or other algorithms that models/includes system response in the reconstruction.

In some embodiments, a QC tool is provided for the evaluation of pixel performance variation on system performance, image quality and quantitation. The QC tool provides loading of the pixel performance map measured on a workstation system and using the map to run typical analysis on system performance, image quality and quantitation. The QC tool also provides for manually modifying the pixel performance map to simulate different pixel performance variation impact scenarios for digital PET. The QC tool can use simulated data or data acquired on the system for the system performance, image quality and quantitation analysis, including count performance, resolution, contrast, noise, uniformity, SUV, etc. The QC tool provides qualitative and quantitative results for users to evaluate system performance against the requirements, helping users understand if the system is still suitable for use when some large pixel performance variation is detected.

While described with reference to digital PET, the following approaches are is applicable to any type of imaging employing detectors having detector pixels, e.g. digital PET, transmission computed tomography (CT), digital single photon emission computed tomography (SPECT), or digital radiography (DR) (that is, flat-panel x-ray with a flat pixelated digital x-ray detector).

Figure 1:
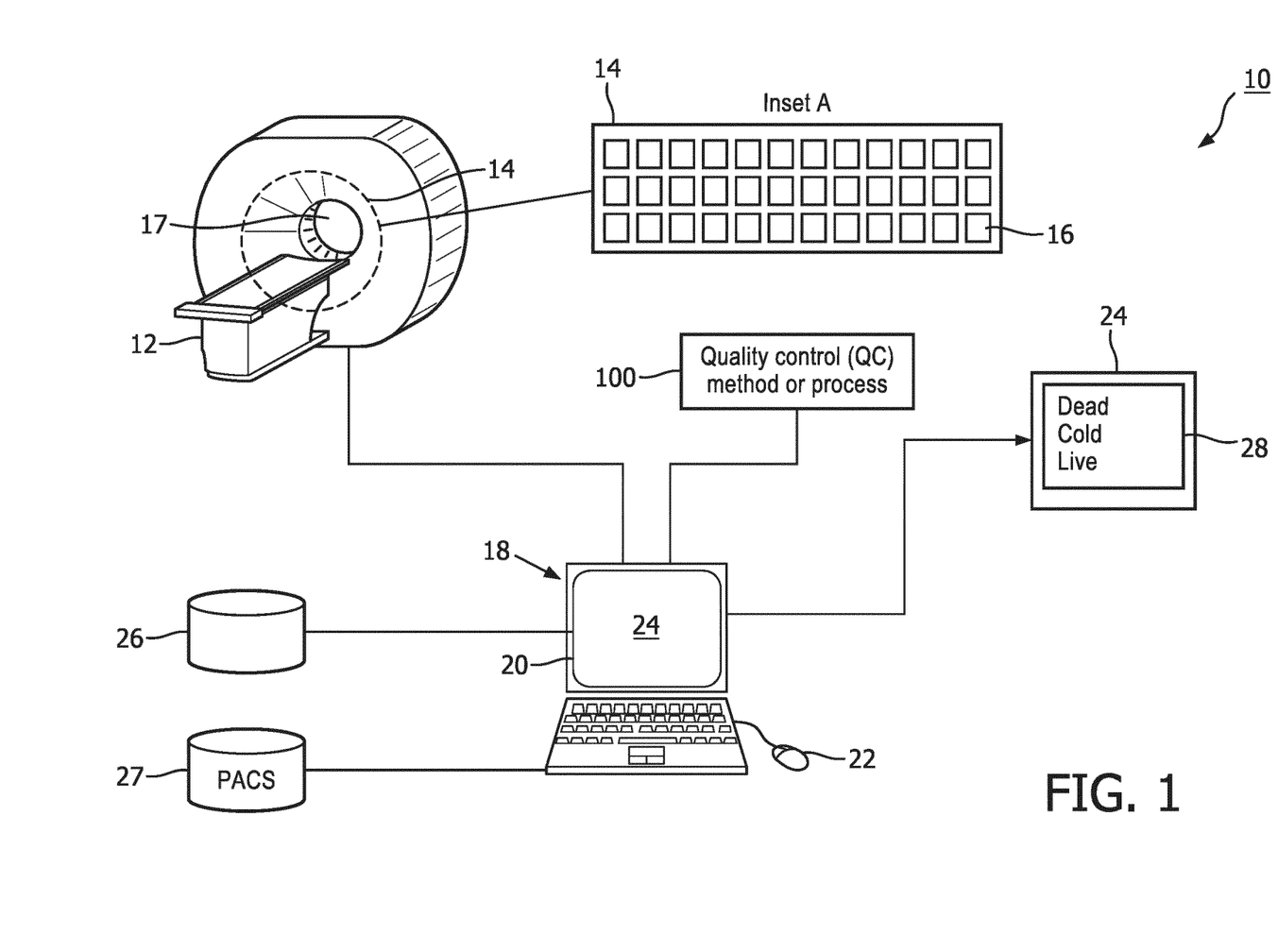
FIG. 1 diagrammatically shows image reconstruction system according to one aspect.

With reference to FIG. 1, an illustrative medical imaging system 10 is shown. As shown in FIG. 1, the system 10 includes an image acquisition device 12. In one example, the image acquisition device 12 can comprise an emission imaging device (e.g., a positron emission tomography (PET) device, a gamma camera for use in single photon emission computed tomography (SPECT), and the like); however, it will be appreciated that any other suitable imaging modality (e.g., transmission computed tomography (CT), X-ray, and the like, as well as hybrid systems, such as PET/CT) may be used. The image acquisition device 12 includes a pixelated detector 14 having a plurality of detector pixels 16 (shown as Inset A in FIG. 1) arranged to collect imaging data from a patient disposed in an examination region 17. Depending on the modality of the image acquisition device 12, the pixelated detector 14 can be a detector ring of a PET device (e.g., an entire PET detector ring or a portion thereof, such as a detector tile, a detector module, and so forth); a detector array of a CT device; a detector of a gamma camera array configured to perform SPECT; and a digital detector array of a digital radiography device such as an X-ray machine.

The system 10 also includes a computer or workstation or other electronic data processing device 18 with typical components, such as at least one electronic processor 20, at least one user input device (e.g., a mouse, a keyboard, a trackball, and/or the like) 22, and a display device 24. In some embodiments, the display device 24 can be a separate component from the computer 18. The workstation 18 can also include one or more databases 26 (stored in a non-transitory storage medium such as RAM or ROM, a magnetic disk, or so forth), and/or the workstation can be in electronic communication with one or more databases 27 (e.g., an electronic medical record (EMR) database, a picture archiving and communication system (PACS) database, and the like). As described herein the database 27 is a PACS database.

The at least one electronic processor 20 is operatively connected with a non-transitory storage medium (not shown) that stores instructions which are readable and executable by the at least one electronic processor 20 to perform disclosed operations including performing a quality control (QC) method or process 100. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the QC method or process 100 may be performed by cloud processing. The QC method or process 100 is performed on a relatively frequent basis as compared with the detector normalization process. For example, in some embodiments the QC method or process 100 is performed on a daily basis, for example in the morning during startup of the imaging device. After performing the QC process 100, the imaging device is then used to perform clinical imaging of patients each loaded in turn into the examination region 17 for imaging and then unloaded to admit the next clinical patient.

Figure 2:
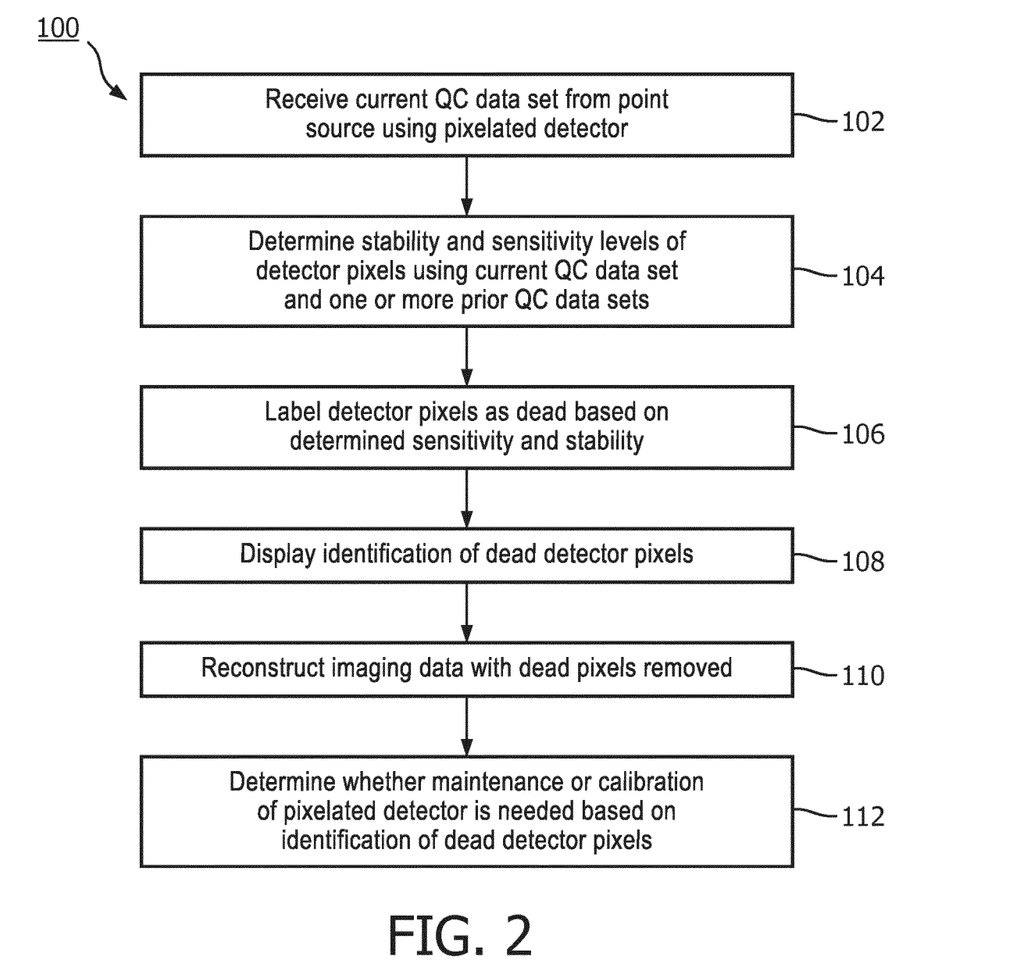
FIG. 2 shows an exemplary flow chart operation of the system of FIG. 1.

With reference to FIG. 2, an illustrative embodiment of the QC method 100 is diagrammatically shown as a flowchart. To start the process, a standard point source phantom is loaded into the examination region 17, preferably at the isocenter of the imaging region 17. For PET calibration, a typical standard point source phantom is a NEMA-standard $^{22}$Na point source. At 102, the at least one electronic processor 20 is programmed to receive a current quality control (QC) data set acquired from the point source by the pixelated detector 14. The QC method 100 also has access to one or more prior QC data sets acquired by the pixelated detector at earlier times, e.g. on past days. The prior QC data sets may, for example, be stored in the database 26. The QC data (e.g., coincidence data or singles data) acquired of the point source is indicative of individual performance of the detector pixels 16, and can be collected on a daily basis. As the point source has a standard radioactivity, e.g. measured in Bq, the counts acquired by all detectors should be approximately the same after considering the distance from the point source to the detector pixels, assuming they have identical sensitivity. For example, in multi-ring PET detectors, a point source at an isocenter of the image acquisition device 12 leads to different distance to the detector pixels 16 at different pixelated detectors 14, leading to a systematic sensitivity difference. At the same time, as there are many geometrical symmetries in the typical PET detector ring with respect to the center of the field of view and source location, equivalently positioned detector pixels are expected to have similar sensitivity. Thus, differences in counts in the current QC data set is indicative of different pixel sensitivities. Other information about detector pixel performance can also be determined. The performance data of the detector pixels 16 can include one or more of sensitivity, energy resolution, time-of-flight (TOF) shift (i.e. detector time delay), and the like. Instead of the mentioned $^{22}$Na point source, in some embodiments, the current QC data and the prior QC data sets are acquired of a reference source comprising a line radiation source from the pixelated detector 14. A line source can provide more uniform irradiation for a multi-ring PET detector. Once received, the acquired QC data (both current and prior) can be saved in the database 26.

At 104, the at least one electronic processor 20 is programmed to determine sensitivity and stability levels of detector pixels 16 of the pixelated detector 14 from the current QC data set and the one or more prior QC data sets. To do so, sensitivity levels of the detector pixels 16 are determined for each QC data set (e.g. the current QC data set and each prior QC data set) based on the ratio of the actual counts acquired by a detector pixel versus the expected counts (expected based on the radioactivity of the point or line source, and/or the average counts of all detectors). The processor 20 determines whether the determined sensitivity level of the detector pixels 16 is outside of a sensitivity threshold range. A "hot" pixel may be defined as having sensitivity higher than an upper threshold; whereas, a "cold" pixel may be defined as having sensitivity below a lower threshold. A pixel with sensitivity between the lower and upper thresholds is deemed to be a normal pixel.

Detector pixel stability is determined as the change over time of the sensitivity of the detector pixel in the current and prior QC data sets. Since a QC data set is typically acquired on a daily basis, it is straightforward to determine the stability, that is, the sensitivity as a function of time, with a "per day" temporal interval. An unstable detector pixel is one whose sensitivity variation over time is unacceptably large. For example, detector pixels 16 are identified having a large sensitivity variation as a function of time (e.g., one day the sensitivity is 10% of the average, and another day 60% of the average, and so forth). It should be noted that a detector pixel could be classified as "normal" in the sense that its sensitivity as determined from the current QC data set is between the lower and upper thresholds, and yet be classified as "unstable" if its sensitivity varies significantly from day to day as determined from the past and current QC data sets (even if this day-to-day variation remains within the lower and upper thresholds).

At 106, the at least one electronic processor 20 is programmed to label at least one of the detector pixels 16 of the pixelated detector 14 as "dead" when the sensitivity level determined for the detector pixel is outside of a sensitivity threshold range (e.g., having a lower limit of less than 20% of the average sensitivity and having a higher limit of greater than 140% of the average sensitivity), and the remaining detector pixels are labeled as "live". For example, the "hot" detector pixels 16 is labeled as dead when the determined sensitivity level is above a maximum sensitivity threshold of the sensitivity threshold range. The "cold" detector pixels 16 are labeled as dead when the determined sensitivity levels is below a minimum sensitivity threshold of the sensitivity threshold range. In a further example, one or more detector pixels 16 previously labeled as dead can be re-labeled as live when the detected stability level of the one or more detector pixels previously labeled as dead is within the stability threshold range.

Furthermore, in the operation 106 the at least one electronic processor 20 is programmed to label at least one of the detector pixels 16 of the pixelated detector 14 as "dead" when the stability level determined for the detector pixel is outside of a stability threshold range. For example, the stability threshold range may be a change in sensitivity of no more than 20% over the past five days, as a non-limiting illustrative example. Using this example, if a detector pixel has measured sensitivity for the past five days (including the current day) of: 70%; 65%; 60%; 62%; 72% then this pixel is deemed to satisfy the 20% stability threshold range. By contrast, a detector pixel having measured sensitivity for the past five days (including the current day) of: 52%, 70%; 75%; 79%; 71% would be deemed to be instable since its sensitivity has ranged between 52% and 79% (a range of 27%, larger than the 20% stability threshold range). This pixel would be labeled as dead due to its instability, even though the measured sensitivities all fall well within the sensitivity threshold range (20%-140%). Alternatively, there may some second pass statistical steps that can be taken before determining it is dead; for example, single outliers in the QC data may be excluded, and/or a second pass assessment may include increasing the number of QC data points used, considering the statistical variance, a combination thereof, or so forth.

In the previous example, a pixel is labeled as dead if it fails either the sensitivity threshold range or the stability threshold range. In another embodiment, the stability assessment is used to retain some stable pixels which would ordinarily be labeled as dead. In one such example, the cold detector pixels 16 are labeled as live, and included in further data processing operations, if they satisfy the stability threshold range. By contrast, in this example hot pixels are labeled as dead even if they are stable. The rationale for this approach is that cold pixels which are stable are still providing useful counts of radiation detection events; whereas, hot pixels which are stable are unreliable since the high sensitivity is likely due a high dark count rate which is unrelated to radiation detection events.

Retention of cold, but stable, detector pixels has substantial advantages, especially in the case of low counts imaging. For example, for point source scans or patient scans with very small foci, if the counts from such cold pixels are excluded, then pixel filling approaches may be taken to estimate the counts associated with such pixels. The pixel filling approaches, however, may introduce error/bias to the data if the filling is using the average or extrapolation of the neighboring pixels. This is especially true if the pixels are clustered, for which the spatial resolution loss will be also significant. Using the counts from the cold (but stable) detector pixels 16 with the corresponding performance map preserves accuracy of the data (including spatial resolution) and overcome a slightly higher noise level associated with the cold pixels.

The output of the detector pixel assessment at 104, 106 operating on the current and prior QC data sets may be variously used, as described next.

At 108, in one application the at least one electronic processor 20 is programmed to control the display device 22 to display an identification 28 of the detector pixels 16 labelled as dead. The identification can be displayed in any suitable format, such as a list, a detector map, and the like. In some examples, the identification 28 can display a map of the detector 14 with pixels labeled as dead marked using filled boxes and live pixels marked using unfilled boxes. A listing of the dead pixels may additionally or alternatively be provided. In some embodiments, the map may differently mark those pixels labeled as dead due to being outside of the sensitivity threshold range versus those pixels labeled as dead due to being outside of the stability threshold range. Alternatively, two different detector maps may be shown (for out of sensitivity range and for unstable pixels). While this type of presentation may be useful, it has a potential disadvantage in that the clinician may have difficulty understanding how the mapped dead pixels practically impacts the clinical images. Due to this uncertainty as to the practical clinical effect of dead pixels, it is possible that the clinician may order a service call when it is not (yet) needed. Conversely, if the clinician underestimates the practical clinical effect of dead pixels then the imaging system may continue to be used for clinical imaging when it would be preferable to service the detector 14.

At 110, in another application, the effect of dead pixels on actual clinical images is presented. To this end, the at least one electronic processor 20 is programmed to reconstruct acquired or simulated imaging data with and without the dead pixels, so as to demonstrate the impact of the dead pixels in the clinical image space. In one example, the processor 20 is programmed to simulate imaging data that would be acquired for an imaging subject by the pixelated detector 14, e.g. using simulation. Two image reconstructions are performed. The first is performed using all simulated imaging data (referred to here as the "reference image"). The reference image can be generated from data in the prior QC data sets, including data acquired with previously labeled dead pixels, image reconstructed by omitting previously labeled dead pixels, and the image quality and quantitation have been deemed as satisfactory. The second is performed using all simulated imaging data except with the detector pixels 16 labeled as dead treated as providing no data (referred to here as the "current QC image"). The data simulated to have been acquired by these dead pixels are excluded from further data processing, and the reconstructed process is adjusted based on these excluded pixels. The resulting current QC image and reference image are presented side-by-side on the display or in some other easily perceived comparative format (e.g. toggling between the two images in response to the user pressing a button) so that the clinician can see the impact of the dead pixels on a clinical image).

For a more advanced user, the foregoing simulation might instead be performed for a point or line phantom, with the simulated data again being reconstructed to form current QC and reference images. The simplified geometry of the point or line phantom may provide more informative comparative images for a user with greater understanding of the PET imaging data acquisition and image reconstruction process.

It should be noted that the simulation of the imaging data can be performed once, and stored in the database 26 of the workstation 18. Likewise, the reference image reconstruction using all imaging data may be done once and stored in the database 26 of the workstation 18. Thereafter, performing the operation 110 merely entails performing the current QC image reconstruction using the stored simulation data with the current set of dead pixels omitted.

The presentation(s) at 108, 110 may be passively presented to the user. In another approach, the QC process 100 may additionally perform active diagnostics on these results to provide maintenance recommendations. Thus, at 112, the at least one electronic processor 20 is programmed to determine whether maintenance or calibration of the pixelated detector 14 is indicated based on the detector pixels 16 labeled as dead. For example, if a large number of detector pixels 16 are labeled as dead, then the pixelated detector 14 may need to be re-calibrated. If, after the calibration process, a large number of detector pixels 16 are still labeled as dead, then a maintenance order can be requested to replace the pixelated detector 14. In this instance, the display device 20 displays a message indicating a recommendation of performing maintenance of the pixelated detector 14 or a recommendation of performing a calibration of the pixelated detector 14 in accord with the determination of whether maintenance or calibration of the pixelated detector 14 is indicated. This operation allows users to systematically evaluate the impact of the dead detector pixels 16, including system count performance, resolution, image quality and quantitation in NEMA studies, patient studies, and the like.

In another example, the processor 20 is programmed to perform the recommendation operation 112 using the reconstructed images produced at 110. Based on the comparison of the current QC image and the reference image, the processor 20 determines whether maintenance or calibration of the pixelated detector 14 is indicated as being needed. In this instance, the display device 20 displays a message indicating a recommendation of performing maintenance of the pixelated detector 14 or a recommendation of performing a calibration of the pixelated detector 14 in accord with the determination of whether maintenance or calibration of the pixelated detector 14 is indicated.

Figure 3:
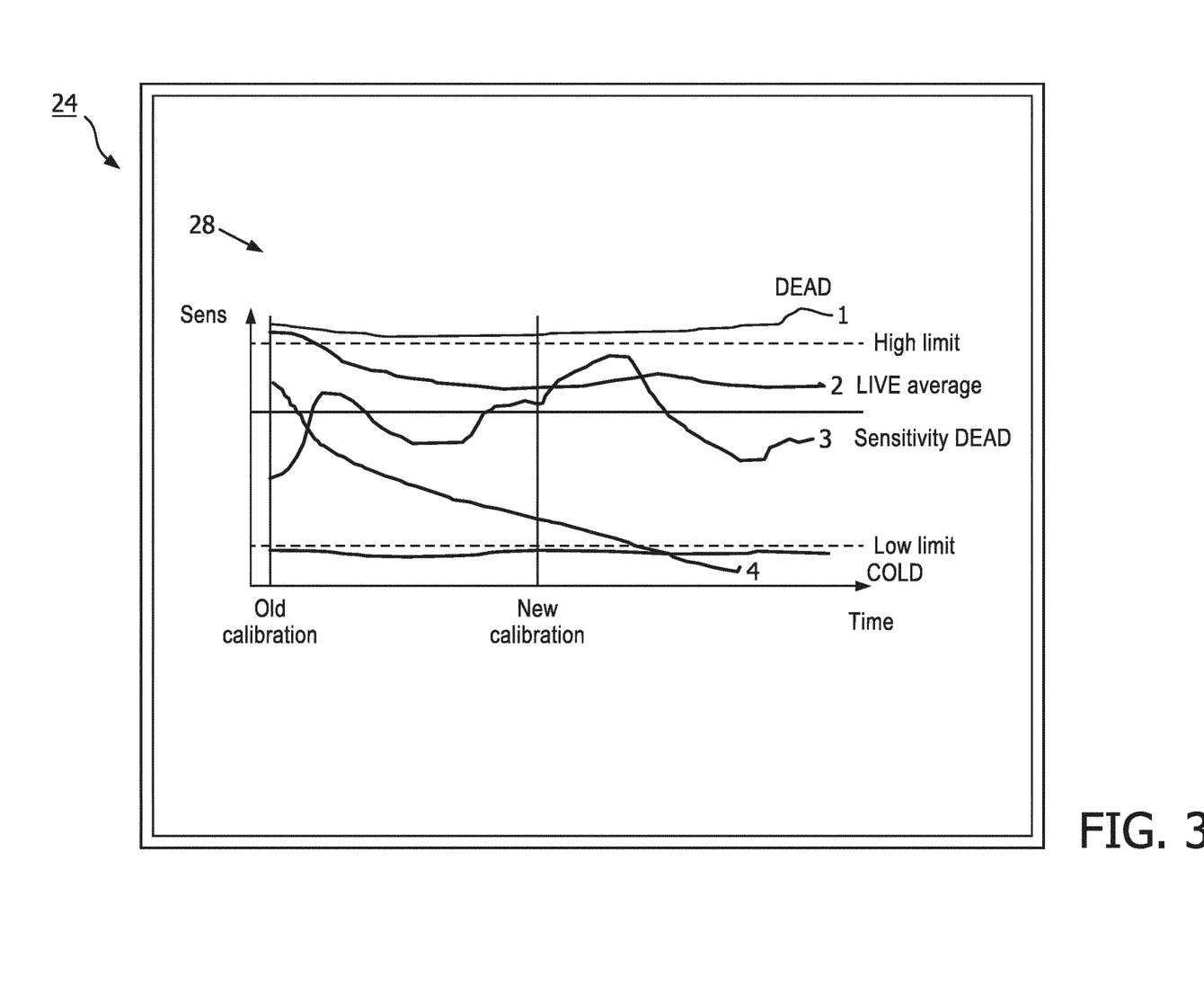
FIG. 3 illustratively shows an identification of detector pixels on a display of the system of FIG. 1.

FIG. 3 shows an example of the display device 20 displaying an indication of the identification 28 of the detector pixels 16. The identification 28 shows a sensitivity vs. time relationship between different classifications of detectors pixels 16. A first curve 1 shows a sensitivity of a detector pixel 16 is above the maximum sensitivity threshold. In one embodiment, this pixel is labeled as "dead" because all hot pixels are labeled as "dead" regardless of stability under the rationale that the high sensitivity is likely due a high dark count rate which is unrelated to radiation detection events. A second curve 2 shows a detector pixel 16 in which the performance thereof stabilizes to within the acceptable sensitivity threshold range after the original calibration problem. A third curve 3 shows a detector pixel 16 that is within the sensitivity threshold range, but the sensitivity thereof varies significantly at different times. If this pixel is thus determined to be unstable, then it is labeled as "dead" even though its sensitivity is within the acceptable range. A fourth curve 4 shows a detector pixel 16 that is below the minimum sensitivity threshold limit (i.e. "cold"), but the performance thereof is stable. This stable detector pixel 16 may also be used in the reconstruction operations, under the rationale that cold pixels which are stable are still providing useful counts of radiation detection events. A fifth curve 5 shows a detector pixel 16 with a sensitivity that decreases significantly. This detector pixel 16 is identified as at risk, and can continue to fail after another calibration process. As this pixel exhibits incipient instability due to its continually decreasing sensitivity, and eventually decreases below the lower threshold (transitions to a "cold" pixel) it is ultimately relabeled as "dead". In this case, a warning is triggered for preventive check/maintenance before the scheduled maintenance, thereby improving system reliability. The service may include replacing modules, or, where dead pixels are occurring in clusters, the detector tiles or modules may be rearranged to break up these clusters and improve overall performance.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory computer-readable medium storing instructions readable and executable by a workstation including at least one electronic processor to perform a quality control (QC) method, the method comprising:
receiving a current QC data set acquired by a pixelated detector and one or more prior QC data sets acquired by the pixelated detector;
determining stability levels of detector pixels of the pixelated detector over time from the current QC data set and the one or more prior QC data sets, wherein a stability level of the detector pixel is determined based on a change of a sensitivity of the detector pixel between the current QC data set and the one or more prior QC data sets;
labeling a detector pixel of the pixelated detector as dead when the stability level determined for the detector pixel is outside of a stability threshold range; and
displaying, on a display device operatively connected with the workstation, an identification of the detector pixels labelled as dead.

2. The non-transitory computer-readable medium of claim 1, wherein the method further includes:
determining sensitivity levels of the detector pixels of the pixelated detector from the current QC data set; and
labeling a detector pixel of the pixelated detector as dead when the sensitivity level is above a maximum sensitivity threshold.

3. The non-transitory computer-readable medium of claim 2, wherein the method further includes:
labeling a detector pixel of the pixelated detector as cold when the sensitivity level is below a minimum sensitivity threshold and has a stable sensitivity level over time;
wherein the display also includes identification of the detector pixels labeled as cold.

4. The non-transitory computer-readable medium of claim 2, wherein the method further includes:
labeling a detector pixel of the pixelated detector as dead when the sensitivity level is below a minimum sensitivity threshold.

5. The non-transitory computer-readable medium of claim 1, wherein the method further includes:
determining whether maintenance or calibration of the pixelated detector is indicated based on the detector pixels labeled as dead;
wherein the display on the display device further includes a message indicating a recommendation of performing maintenance of the pixelated detector or a recommendation of performing a calibration of the pixelated detector in accord with the determination of whether maintenance or calibration of the pixelated detector is indicated, the message further indicating a recommendation to rearrange a cluster of detector pixels labeled as dead in the pixelated detector.

6. The non-transitory computer-readable medium of claim 1, wherein the operation of labeling a detector pixel of the pixelated detector as dead when the stability level determined for the detector pixel is outside of a stability threshold range further includes:
re-labeling one or more detector pixels previously labeled as dead as live when the detected stability level of the one or more detector pixels previously labeled as dead is within the stability threshold range.

7. The non-transitory computer-readable medium of claim 1, wherein the method further includes:
simulating imaging data acquired for an imaging subject by the pixelated detector with the detector pixels labeled as dead treated as providing no data; and
reconstructing the simulated imaging data to generate a simulated image.

8. The non-transitory computer-readable medium of claim 1, wherein the method further includes:
reconstructing an imaging data set acquired by the pixelated detector with data acquired by the detector pixels labeled as dead omitted to generate a current QC image; and
displaying, on the display device a comparison of the current QC image with a reference image generated with the one or more prior QC data sets.

9. The non-transitory computer-readable medium of claim 8, wherein the method further includes:
comparing the current QC image and the reference image;
determining whether maintenance or calibration of the pixelated detector is indicated based on the comparison of the current QC image and the reference image;
wherein the display on the display device further includes a message indicating a recommendation of performing maintenance of the pixelated detector or a recommendation of performing a calibration of the pixelated detector in accord with the determination of whether maintenance or calibration of the pixelated detector is indicated.

10. An imaging system, comprising:
an image acquisition device configured to acquire imaging data of a patient, the image acquisition device including a pixelated detector with a plurality of detector pixels;
a display device; and
at least one electronic processor programmed to:
receive a current quality control (QC) data set acquired by the pixelated detector and one or more prior QC data sets acquired by the pixelated detector;
determine stability levels of the detector pixels over time from the current QC data set and the one or more prior QC data sets, wherein a stability level of the detector pixel is determined based on a change of a sensitivity of the detector pixel between the current QC data set and the one or more prior QC data sets;
label one or more of the detector pixels as dead when the stability level determined for the detector pixels is outside of a stability threshold range; and
control the display device to display an identification of the detector pixels labelled as dead.

11. The imaging system of claim 10, wherein the at least one electronic processor is further programmed to:
determine sensitivity levels of the detector pixels of the pixelated detector from the current QC data set;
label a detector pixel of the pixelated detector as dead when the sensitivity level is above a maximum sensitivity threshold;
label a detector pixel of the pixelated detector as cold when the sensitivity level is below a minimum sensitivity threshold
control the display device to display the identification of the pixels as dead or cold.

12. The imaging system of claim 10, wherein the at least one electronic processor is further programmed to:
determine whether maintenance or calibration of the pixelated detector is indicated based on the detector pixels labeled as dead;

wherein the display on the display device further includes a message indicating a recommendation of performing maintenance of the pixelated detector or a recommendation of performing a calibration of the pixelated detector in accord with the determination of whether maintenance or calibration of the pixelated detector is indicated.

13. The imaging system of claim 10, wherein the at least one electronic processor is further programmed to:
re-label one or more detector pixels previously labeled as dead as live when the detected stability level of the one or more detector pixels previously labeled as dead is within the stability threshold range.

14. The imaging system of claim 10, wherein the at least one electronic processor is further programmed to:
simulate imaging data acquired for an imaging subject by the pixelated detector with the detector pixels labeled as dead treated as providing no data; and
reconstruct the simulated imaging data to generate a simulated image.

15. The imaging system of claim 10, wherein the at least one electronic processor is further programmed to:
reconstruct an imaging data set acquired by the pixelated detector with data acquired by the detector pixels labeled as dead omitted to generate a current QC image; and
control the display device to display a comparison of the current QC image with a reference image generated from the one or more prior QC data sets.

16. The imaging system of claim 15, wherein the at least one electronic processor is further programmed to:
compare the current QC image and the reference image;
determine whether maintenance or calibration of the pixelated detector is indicated based on the comparison of the current QC image and the reference image;
wherein the display on the display device further includes a message indicating a recommendation of performing maintenance of the pixelated detector or a recommendation of performing a calibration of the pixelated detector in accord with the determination of whether maintenance or calibration of the pixelated detector is indicated.

17. The imaging system of claim 10, wherein the pixelated detector is one of:
a detector ring of a position emission tomography (PET) device; a detector array of a transmission computed tomography (CT) device; a detector of a gamma camera configured to perform single photon emission computed tomography (SPECT); and a digital detector array of a digital radiography device.

18. The imaging system of claim 10, wherein the current and one or more prior QC data sets are acquired of a reference source comprising a point or line radiation source.

19. An imaging system, comprising:
a positron emission tomography (PET) device configured to acquire imaging data of a patient, the image acquisition device including a PET detector ring with a plurality of PET detector pixels;
a display device; and
at least one electronic processor programmed to:
receive a current quality control (QC) data set acquired by the pixelated detector and one or more prior QC data sets acquired by the pixelated detector;
determine sensitivity levels of the detector pixels from the current QC data set;
determine stability levels of the detector pixels over time from the current QC data set and the one or more prior QC data sets, wherein a stability level of the detector pixel is determined based on a change of a sensitivity of the detector pixel between the current QC data set and the one or more prior QC data sets;
label a detector pixel of the pixelated detector as dead when the sensitivity level is above a maximum sensitivity threshold;
label a detector pixel of the pixelated detector as cold when the sensitivity level is below a minimum sensitivity threshold; and
control the display device to display an identification of the detector pixels labelled as dead or cold.

20. The imaging system of claim 19, wherein the at least one electronic processor is further programmed to:
re-label one or more detector pixels previously labeled as dead as live when the detected stability level of the one or more detector pixels previously labeled as dead is within the maximum and minimum stability thresholds.

* * * * *